US011771340B2

(12) United States Patent
Handshaw et al.

(10) Patent No.: US 11,771,340 B2
(45) Date of Patent: Oct. 3, 2023

(54) DETECTION OF MEDICALLY RELATED EVENTS AT A POINT OF SALE

(71) Applicant: ZEBRA TECHNOLOGIES CORPORATION, Lincolnshire, IL (US)

(72) Inventors: Darran Michael Handshaw, Sound Beach, NY (US); Yuri Astvatsaturov, Lake Forest, IL (US); Edward Barkan, Miller Place, NY (US)

(73) Assignee: Zebra Technologies Corporation, Lincolnshire, IL (US)

( * ) Notice: Subject to any disclaimer, the term of this patent is extended or adjusted under 35 U.S.C. 154(b) by 538 days.

(21) Appl. No.: 17/036,324

(22) Filed: Sep. 29, 2020

(65) Prior Publication Data

US 2022/0095951 A1 Mar. 31, 2022

(51) Int. Cl.
*A61B 5/08* (2006.01)
*A61L 2/10* (2006.01)
*G06T 7/00* (2017.01)
*G07G 1/01* (2006.01)
*A61L 2/22* (2006.01)
*A61B 5/00* (2006.01)

(52) U.S. Cl.
CPC .......... *A61B 5/0823* (2013.01); *A61B 5/0077* (2013.01); *A61B 5/4803* (2013.01); *A61B 5/7285* (2013.01); *A61L 2/10* (2013.01); *A61L 2/22* (2013.01); *G06T 7/0012* (2013.01); *G07G 1/01* (2013.01); *A61G 2202/25* (2013.01)

(58) Field of Classification Search
CPC ... A61B 5/0823; A61B 5/0077; A61B 5/4803; G06T 7/0012; G07G 1/00
See application file for complete search history.

(56) References Cited

U.S. PATENT DOCUMENTS

2020/0093459 A1* 3/2020 Rahman ............... A61B 5/7275

* cited by examiner

*Primary Examiner* — Sean E Conley
*Assistant Examiner* — Justin Hwang
(74) *Attorney, Agent, or Firm* — Yuri Astvatsaturov

(57) ABSTRACT

Systems and methods for detecting medically related events at a point of sale are disclosed herein. An example method of detecting droplets associated with a sneeze or cough at a point of sale includes: capturing, by an image sensor associated with a checkout workstation, one or more images; analyzing, by one or more processors, the images captured by the image sensor associated with the checkout workstation, to detect an indication that one or more droplets associated with a sneeze or cough are present upon one or more equipment associated with the checkout workstation; and triggering, by the one or more processors, a disinfection of the checkout workstation responsive to detecting the indication that the one or more droplets associated with the sneeze or cough are present upon the one or more equipment associated with the checkout workstation.

32 Claims, 9 Drawing Sheets

400

402
Capture one or more images by image sensor associated with checkout workstation

404
Analyze images captured by image sensor associated with checkout workstation to detect indication that droplets associated with sneeze or cough are present upon equipment associated with checkout workstation

406
Trigger disinfection of checkout workstation

500

502
Capture one or more images of individual within threshold proximity of checkout workstation

504
Analyze images captured by image sensor of individual within threshold proximity of checkout workstation to detect motion indicative of sneeze or cough

506
Trigger disinfection of checkout workstation

DETECTION OF MEDICALLY RELATED EVENTS AT A POINT OF SALE

BACKGROUND

Various diseases (including viruses such as COVID-19) are transmitted via exhaled droplets from infected individuals. In particular, infected individuals who sneeze or cough (or even speak or simply exhale) may spray such droplets in many directions, especially if an infected individual is not covering his or her nose and/or mouth with a face covering. In a retail environment, droplets exhaled by a user of point of sale (POS) equipment, such as retail checkout workstations and their components, can settle on the POS equipment and cause the disease to be transmitted to the next user of the POS equipment.

SUMMARY

In an embodiment, the present invention is a method, comprising: capturing, by an image sensor associated with a checkout workstation, one or more images; analyzing, by one or more processors, the images captured by the image sensor associated with the checkout workstation, to detect an indication that one or more droplets associated with a sneeze or cough are present upon one or more equipment associated with the checkout workstation; and triggering, by the one or more processors, a disinfection of the checkout workstation responsive to detecting the indication that the one or more droplets associated with the sneeze or cough are present upon the one or more equipment associated with the checkout workstation.

In another embodiment, the present invention is a method, comprising: capturing, by an image sensor associated with a checkout workstation, one or more images; analyzing, by one or more processors, the images captured by the image sensor associated with the checkout workstation, to detect an indication that one or more droplets associated with a sneeze or cough are present upon one or more equipment associated with the checkout workstation; and triggering, by the one or more processors, responsive to detecting the indication that the one or more droplets associated with the sneeze or cough are present upon the one or more equipment associated with the checkout workstation, an automatic dissemination, by a disinfection device associated with the checkout workstation, of disinfectant over the affected one or more equipment for a threshold period of time for disinfecting the one or more equipment.

In yet another embodiment, the present invention is a method, comprising: capturing, by an image sensor associated with a checkout workstation, one or more images of an individual within a threshold proximity of the checkout workstation; analyzing, by one or more processors, the one or more images to detect a motion, by the individual, indicative of a sneeze or cough; and triggering, by the one or more processors, a disinfection of the checkout workstation responsive to detecting the motion of the individual indicative of the sneeze or cough.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

FIG. 2A illustrates refraction of light through the window when there are no droplets or particles present on the window, while FIG. 2B illustrates refraction of light through the window when there is at least one droplet present on the window.

FIG. 3A illustrates a window of a checkout workstation including initial threshold contamination, while FIG. 3B illustrates the window of the checkout workstation including droplets in addition to the initial threshold contamination.

Figure 1:
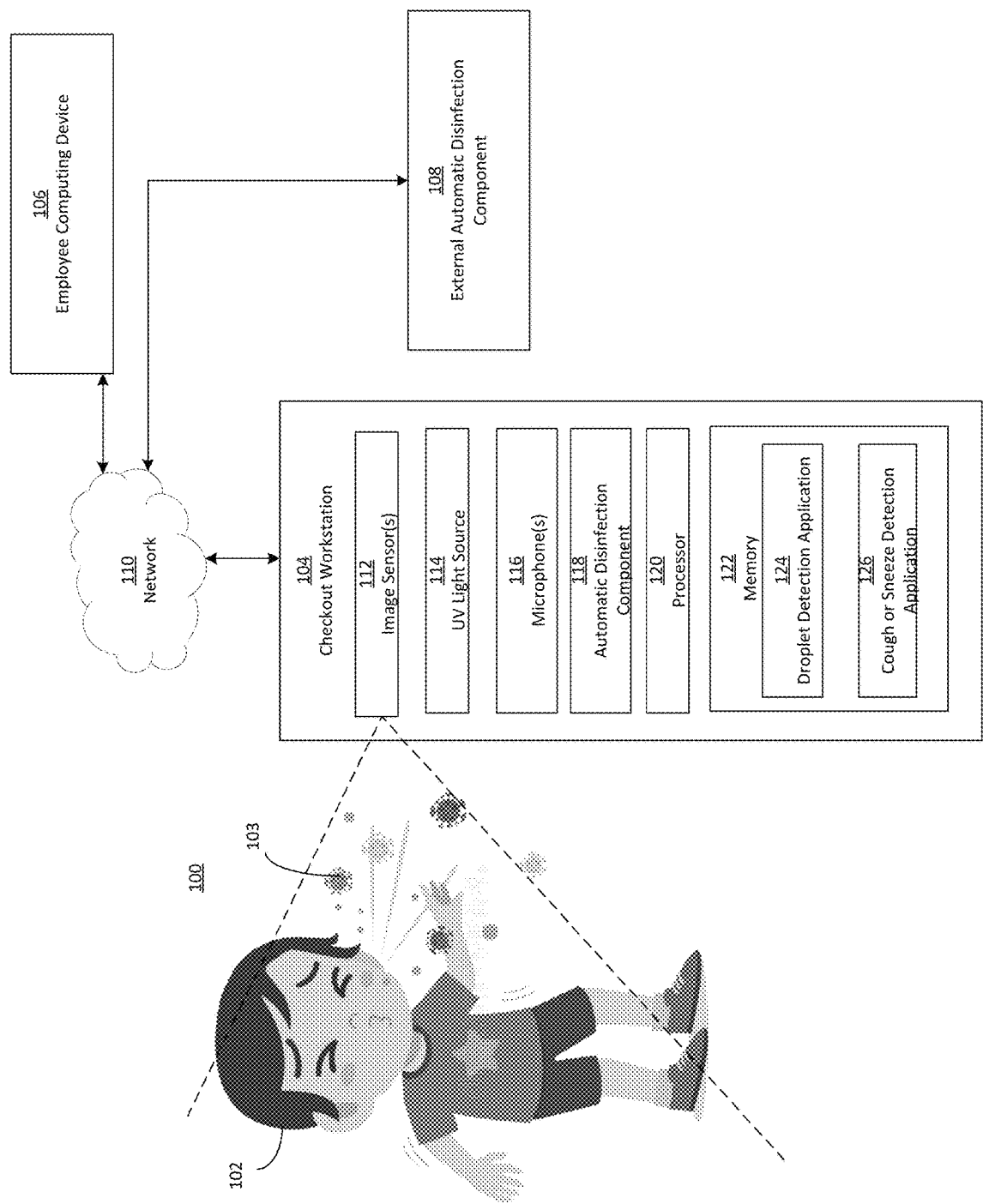
FIG. 1 illustrates a block diagram of an example system including a logic circuit for implementing the example methods and/or operations described herein, including droplet detection methods and/or cough and/or sneeze detection methods.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

The present disclosure provides systems and methods for detecting the occurrence of a cough or sneeze near a checkout workstation that results in the deposition of liquid droplets on the surface of equipment associated with the checkout workstation, and triggering remedial actions to help prevent transmission of disease to the next individual who uses or otherwise touches the equipment associated with the checkout workstation, including, e.g., automatically disinfecting the checkout workstation, alerting an employee who can disinfect the checkout workstation, and/or closing the checkout workstation until it is disinfected (which may be confirmed, e.g., by using 2D image recognition to recognize a spray bottle using 2D image recognition and particles being applied to the window and wiped clean).

An image sensor may be positioned to detect the presence of particles (e.g., liquid droplets) that settle on scanner windows of a checkout workstation. In some examples, the image sensor that is used to detect particles/droplets may be an existing image sensor of the checkout workstation (e.g., an image sensor typically used for capturing images of barcodes or items being purchased), with a field of view that passes through a window of the checkout workstation. For example, the image sensor may constantly or periodically capture images which may be analyzed to detect liquid droplets and/or other particles that are deposited on the equipment associated with the checkout workstation. For instance, detecting the sudden appearance of a large number of such particles in images captured by the image sensor over a short amount of time may be an indication that a sneeze has occurred, and that droplets from the sneeze have settled on the window of the checkout workstation. For instance, in some examples, the presence of these droplets can be detected by cycling a variable-focus image sensor through the focal plane of a checkout workstation window to periodically check the window for particulates and compare real-time images to reference images or images taken prior to the evaluation frames.

Moreover, in some examples, the presence of these droplets can be detected by emitting light through one side of a checkout workstation window, and measuring light on the other side of the checkout workstation window. That is, when there is no foreign matter touching the window, total-internal-reflection can result in a substantial amount of light being passed from one side to the other, but when droplets of saliva are deposited on the window, they interfere with the total-internal-reflection of the glass because they modify the refractive index of the medium with which the glass is in contact, and affect the total amount of light received as the detector. Consequently, reduced light measured on the other side of the checkout workstation window may be correlated with the amount of debris (like droplets) deposited on the window.

In some examples, the image sensor may be activated to detect liquids or particles that are deposited on the equipment associated with the checkout workstation only after receiving an indication that a sneeze or cough has occurred based on data captured by another sensor. That is, in some examples, the image sensor may be activated to detect particles only after a sneeze/cough event is detected in order to avoid activating remedial measures such as disinfecting or closing the checkout workstation in response to dust or debris particles that do not carry disease. An indication that a sneeze or cough has likely occurred may be determined based on detecting motions indicative of sneezes or coughs in images captured by an image sensor positioned to capture images of individuals near the checkout workstation, and/or based on detecting sounds indicative of sneezes or coughs captured by a microphone positioned near the checkout workstation. In some examples, images captured by the image sensor positioned to capture images of individuals near the checkout workstation may be further analyzed to determine whether an individual who makes a motion indicative of sneezing or coughing is wearing a mask. For instance, in some examples, if the individual who sneezes or coughs is wearing a mask, disinfecting or closing the checkout workstation may not be required.

Additionally, in some examples, multiple microphones may be configured to capture sound data near the checkout workstation in order to pinpoint the location of a sound indicative of a sneeze or cough. That is, by comparing the time it takes the sound of the cough or sneeze to travel to a microphone positioned on the left side of the checkout workstation to the time it takes the sound of the cough or sneeze to travel to another microphone positioned on the right side of the checkout workstation, the system may determine whether the cough or sneeze occurred at the front of the checkout workstation (e.g., potentially spraying droplets/particles onto the equipment of the checkout workstation), or off to one side or the other of the checkout workstation (e.g., potentially not spraying droplets/particles onto the equipment of the checkout workstation, or spraying droplets/particles onto the equipment of a different checkout workstation entirely).

In some examples, the microphone- or video-based detection of a cough or sneeze can trigger a variable-focus image sensor to adjust its focal plane to specifically examine the window(s) of the checkout workstation for droplets immediately or shortly after the cough or sneeze is been detected. Furthermore, in some examples, adjusted or alternate illumination and/or image sensor settings can be activated during the droplet detection frames. For instance, illumination and/or image sensor settings can be configured to specifically identify liquid-based depositions on the scanner window. In some examples, adjusting the illumination settings can include activating an ultraviolet (UV) light to cause salivary particles on the window or platter to fluoresce in order to aid in detection (i.e., because certain particles in saliva are fluorescent). The UV light may be activated from inside the window, or along the edges of the window, i.e., in order to minimize the chance of having UV light shined directly in the user's eyes.

Referring now to the drawings, FIG. 1 illustrates a block diagram of an example droplet detection system 100. As shown in FIG. 1, an individual 102 (e.g., a customer or employee associated with the checkout workstation 104) may approach a checkout workstation 104 to complete a transaction, or may otherwise be near the checkout workstation 104, and may cough or sneeze (or even simply talk or breathe), spraying droplets 103 in the direction of the checkout workstation. In some examples, the checkout workstation 104 may be configured to communicate with an employee computing device 106, or an external automatic disinfection component 108, e.g., via a wired or wireless network 110.

The checkout workstation 104 may include one or more image sensor(s) 112, as may be implemented in an imaging assembly. The image sensors 112 may include two-dimensional image sensors, depth image sensors, infrared image sensors, thermal image sensors, image sensors specifically configured to detect light at certain wavelengths, light detectors, or any other suitable image sensors in various examples. In some examples, at least one of the image sensors 112 may be configured such that its FOV passes through a window of the checkout workstation 104, or otherwise includes a product scanning region of the checkout workstation 104, e.g., so that the image sensor 112 may capture images of items to be purchased and/or barcodes associated with items to be purchased. In some examples, at least one of the image sensors 112 may be implemented as part of a variable-focus imaging assembly configured to cycle through (or otherwise shift between) a focal plane for capturing images of droplets present upon a window or other portion of the checkout workstation 104, and a focal plane for capturing images of items to be purchased and/or barcodes associated with items to be purchased. Similarly, in some examples, at least one of the image sensors 112 may be configured to cycle through (or otherwise shift between) exposure settings, gain settings, or illumination settings for capturing images of droplets present upon a window or other portion of the checkout workstation, and different exposure settings, gain settings, or illumination settings for capturing images of items to be purchased and/or barcodes associated with items to be purchased. Moreover, in some examples, at least one of the image sensors 112 may be configured such that its field of view (FOV) includes faces or bodies of individuals who are currently using or are otherwise within a threshold proximity (e.g., six feet, ten feet, or another suitable threshold proximity) of the checkout workstation 104. Additionally, in some examples, at least one of the image sensors 112 may be a component of the checkout workstation 104. Furthermore, in some examples, at least one of the image sensors 112 may be separate from or otherwise external to the checkout workstation 104 (e.g., positioned above the checkout workstation 104 or a group of checkout workstations in a retail environment) and configured to communicate with the checkout workstation 104 via a wired or wireless network, such as the network 110.

Figure 8:
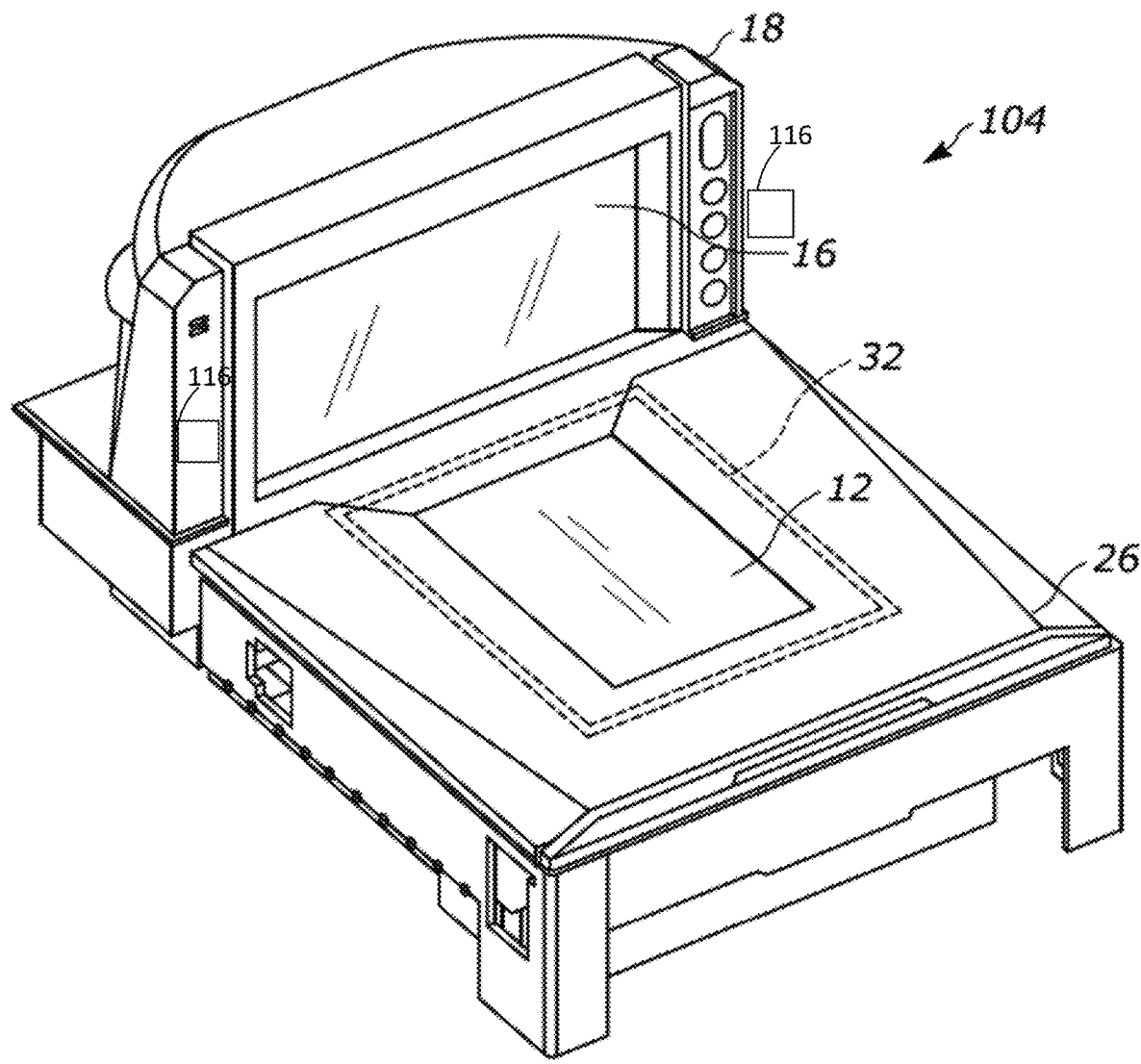
FIG. 8 is a perspective view of the exemplary checkout workstation of FIG. 7 in isolation.

Furthermore, in some examples, the checkout workstation 104 may include one or more microphones 116, which may be positioned at various locations of the checkout workstation 104 and may be configured to capture sound data associated with the checkout workstation 104. In some examples, the microphones 116 may be positioned at opposite sides of the checkout workstation 104, e.g., as shown in FIG. 8 below. In some examples, at least one of the microphones 116 may be separate from or otherwise external to the checkout workstation 104 (e.g., positioned near the checkout workstation 104 or a group of checkout workstations in a retail environment) and configured to communicate with the checkout workstation 104 via a wired or wireless network, such as the network 110.

Additionally, in some examples, the checkout workstation 104 may include an automatic disinfection component 118. For instance, in some examples, the automatic disinfection component 118 may include an ultraviolet (UV) disinfecting light that activates to disinfect the checkout workstation 104. Moreover, in some examples, the automatic disinfection component 118 may include an aerosol spray washer that activates to spray disinfectant over affected areas of the checkout workstation 104 to disinfect the checkout workstation 104. For instance, the automatic disinfection component 118 may include a retractable spray nozzle that activates to spray disinfectant over at least a portion of the checkout workstation 104 and retracts when disinfection is complete. In some examples, the automatic disinfection component 118 may include an automatic wiper arm that activates to disinfect the checkout workstation 104 by wiping it down with disinfectant.

Furthermore, the checkout workstation 104 may include a processor 120 and a memory 122. The processor 120, which may be, for example, one or more microprocessors, controllers, and/or any suitable type of processors, may interact with the memory 122 accessible by the one or more processors 120 (e.g., via a memory controller) to obtain, for example, machine-readable instructions stored in the memory 122 corresponding to, for example, the operations represented by the flowcharts of this disclosure, including those of FIGS. 4, 5, and 6. In particular, the machine-readable instructions stored in the memory 122 may include instructions for executing a droplet detection application 124, and/or a cough or sneeze detection application 126.

Moreover, the machine-readable instructions stored in the memory 122 may include instructions for reading barcodes in images captured by the image sensors 112, identifying items to be purchased depicted in images captured by the image sensors 112, and/or processing transactions for purchasing items.

Generally speaking, executing the droplet detection application 124 may include analyzing images captured by the image sensor 112 to detect when droplets associated with a sneeze or cough (or other exhale) are present upon equipment of the checkout workstation 104 (e.g., a scanner window, a handheld barcode reader, a touch screen window, or any other surface or part of the checkout workstation 104), and, in some instances, triggering a responsive action based on the presence of the droplets on the equipment associated with the checkout workstation 104. Executing the cough and/or sneeze detection application 126 may include analyzing images captured by the image sensor 112 and/or sound data captured by the microphone(s) 116 to detect indications of motions and/or sounds indicative of sneezes or coughs by individuals near the checkout workstation 104, and, in some instances, triggering a responsive action based on the motions and/or sounds indicative of sneezes or coughs by individuals near the checkout workstation 104. In some examples, the droplet detection application 124 and the cough and/or sneeze detection application 126 may operate independently. Moreover, in some examples, the cough and/or sneeze detection application 126's detection of a cough or sneeze may be used by the droplet detection application 124, e.g., as confirmation that any detected droplets or particles will likely be related to a cough or sneeze before capturing or analyzing images, or before triggering the responsive action. Similarly, in some examples, the droplet detection application 124's detection of droplets may be used by the cough and/or sneeze detection application 126, e.g., as confirmation that a detected cough or sneeze produced droplets that landed on equipment associated with the checkout workstation 104 before triggering the responsive action. While the droplet detection application 124 and the cough and/or sneeze detection application 126 are shown as two separate applications in FIG. 1, the functionality described as being performed by each of these applications may be combined into one application or otherwise fewer total applications, or split into more total applications, and additional applications may be included in various embodiments.

In particular, executing the droplet detection application 124 may include (in some examples) analyzing images captured by the image sensor 112 constantly or periodically to detect droplets or particles present in the images. Additionally, in some examples, the droplet detection application 124 may analyze images captured by the image sensor 112 based on receiving an indication that the cough or sneeze detection application 126 has detected a cough or sneeze near the checkout workstation 104.

In examples in which the image sensor 112 is a variable-focus image sensor (e.g., as discussed above, configured to switch or cycle between a focal plane for detecting barcodes and a focal plane for detecting droplets or particles on equipment of the checkout workstation 104), the droplet detection application 124 may analyze images captured by the image sensor 112 when it is using the focal plane for detecting droplets or particles on equipment of the checkout workstation 104. In some examples, the image sensor 112 may switch to a focal plane for detecting droplets or particles on equipment of the checkout workstation 104 based on receiving an indication that the cough or sneeze detection application 126 has detected a cough or sneeze near the checkout workstation 104. Similarly, in examples in which the image sensor 112 is configured to switch or cycle between exposure settings, gain settings, or illumination settings for detecting droplets or particles on equipment of the checkout workstation 104 and exposure settings, gain settings, or illumination settings for capturing images of barcodes or products to be purchased, the droplet detection application 124 may analyze images captured by the image sensor 112 when it is using the exposure settings, gain settings, or illumination settings for detecting droplets or particles. In some examples, the image sensor 112 may switch to exposure settings, gain settings, or illumination settings for detecting droplets or particles on equipment of the checkout workstation 104 based on receiving an indication that the cough or sneeze detection application 126 has detected a cough or sneeze near the checkout workstation 104.

In some examples, the checkout work station 104 may include a UV light source 114, and the droplet detection application 124 may activate the UV light source 114 to shine upon one or more equipment associated with the checkout workstation 104 (e.g., a window of the checkout workstation 104) and may analyze images that are captured by the image sensor 112 while the UV light source 114 is activated in order to detect droplets on the equipment. In particular, research has shown that saliva may fluoresce when exposed to a UV light source. Consequently, images captured by an image sensor 112 configured to detect light at wavelengths at which saliva fluoresces may be analyzed to determine whether particles present on equipment of the checkout workstation 104 include saliva (e.g., as opposed to dirt, dust, water, disinfectant or any other particles or droplets that may be present on the equipment of the checkout workstation 104). In some examples, the droplet detection application 124 may activate the UV light source 114 based on receiving an indication that the cough or sneeze detection application 126 has detected a cough or sneeze near the checkout workstation 104.

In some examples, the droplet detection application 124 may detect that droplets associated with a sneeze or cough are present upon the equipment associated with the checkout workstation 104 based on detecting a change in a refractive index of a window of the checkout workstation 104.

Figure 2A:
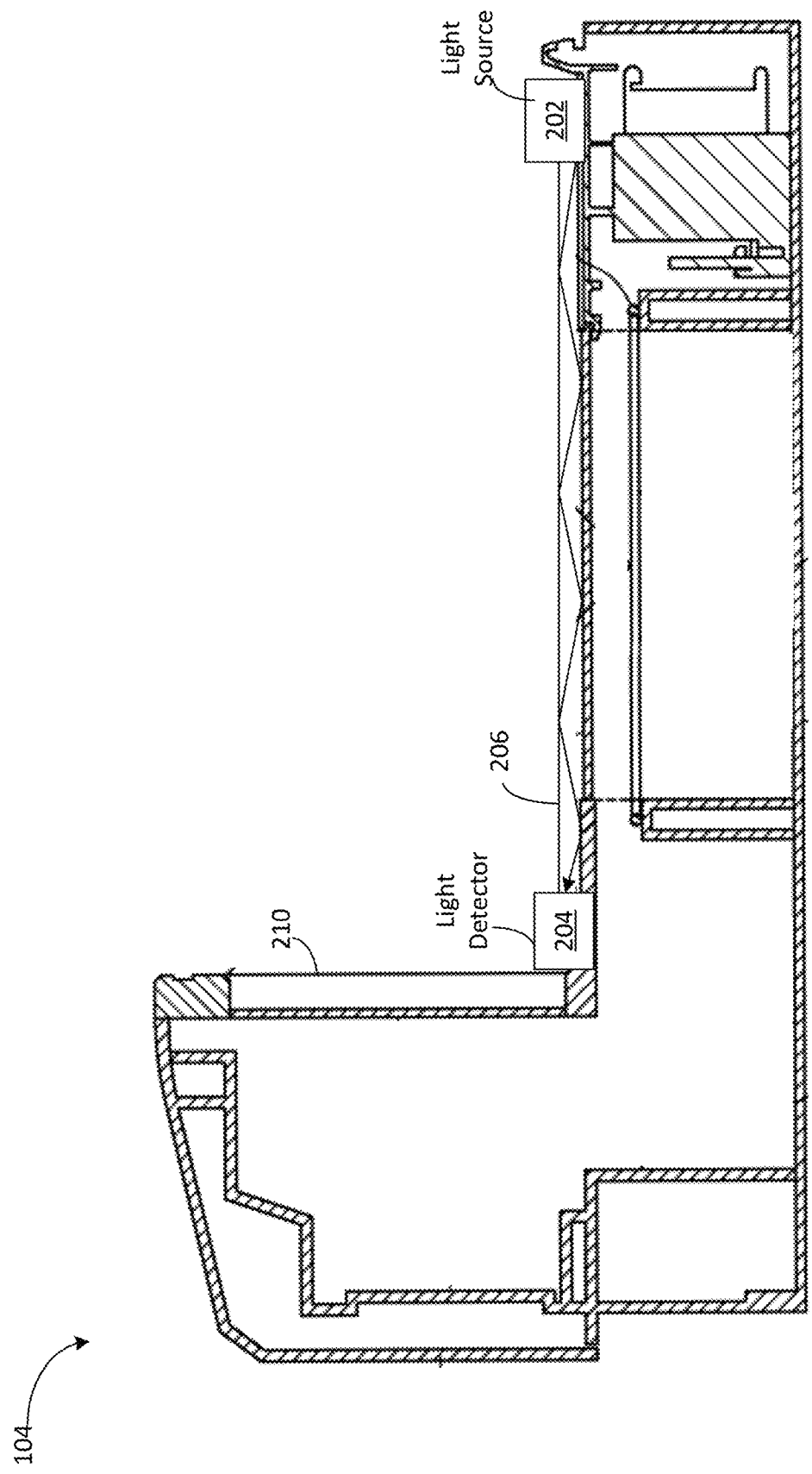
FIGS. 2A and 2B illustrate cross-sectional views of an exemplary bi-optical checkout workstation, including examples of refraction of light through the window of the checkout workstation. In particular.
Figure 2B:
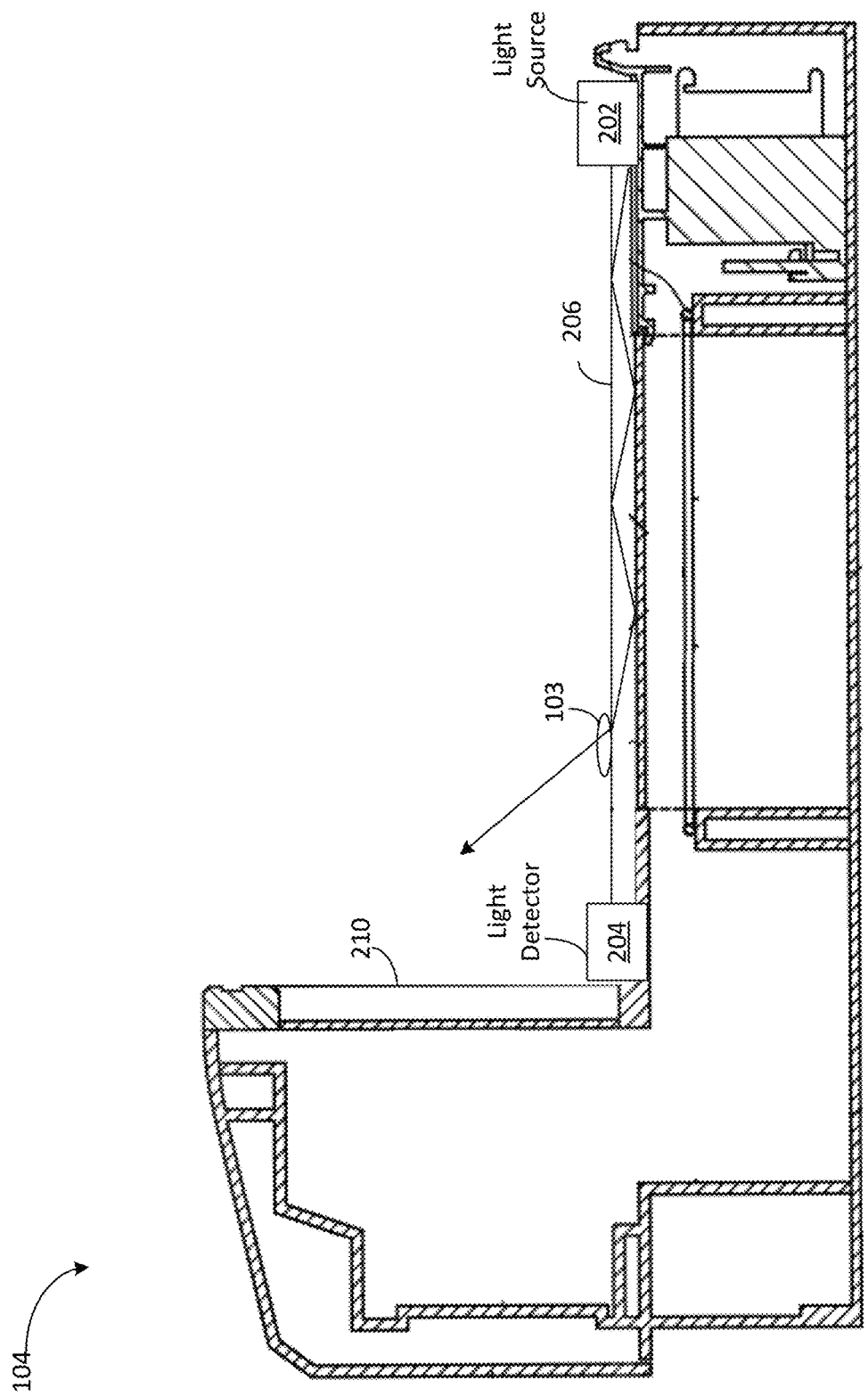

For instance, in an example, as shown in FIGS. 2A and 2B, a light source 202 may be positioned at one side or edge of the window 206 of the checkout workstation 104, and a light detector 204 may be positioned on an opposite side of the window 206 of the checkout workstation 104, e.g., with the light source 202 positioned closer to the user end of the checkout workstation 104 so that escaping light is near the intersection of the window 206 and the other window 210. In this example, the droplet detection application 124 may activate the light source 202 and may measure the light detected by the light detector 204 to determine whether there are droplets or other particles present on the window 206 of the checkout workstation 104. That is, because the presence of droplets 103 on the window 206 of the checkout workstation 104 modifies the refractive index though which light passes as it travels from the light source 202 to the image detector 204 via the window, a reduction in light captured by the light detector 204 may indicate the presence of droplets 103 on the window 206 of the checkout workstation 104.

For instance, FIG. 2A illustrates an example of light passing from a light source 202 to the a light detector 204 (e.g., a photodetector) via a window 206 without any droplets 103 present upon the window 206, while FIG. 2B illustrates an example of light passing from the light source 202 to the light detector 204 via the window 206 when a droplet 103 is present on the window 206. Consequently, because the presence of droplets 103 on the window of the checkout workstation 104 modifies the refractive index though which light passes as it travels from the light source 202 to the light detector 204 via the window 206, a smaller amount of light reaches the light detector 204 in FIG. 2B compared to in FIG. 2A. In some examples, the droplet detection application 124 may activate the light detector 204 based on receiving an indication that the cough or sneeze detection application 126 has detected a cough or sneeze near the checkout workstation 104.

In some examples, the droplet detection application 124 may detect that droplets 103 associated with a sneeze or cough are present upon the equipment associated with the checkout workstation 104 based on comparing control images to images captured by the image sensor 112. For instance, in some examples, when the image sensor 112 captures images of a particular portion of the checkout workstation 104, the control images may be images of that portion of the checkout workstation 104 without any droplets 103 present. Moreover, in some examples, the control images may be prior images captured by the image sensor 112, e.g., images captured prior to the individual 102 being within proximity of the checkout workstation 104, or images captured prior to the droplet detection application 124 receiving an indication, from the cough or sneeze detection application 126, that a cough or sneeze has been detected near the checkout workstation 104.

Figure 3B:
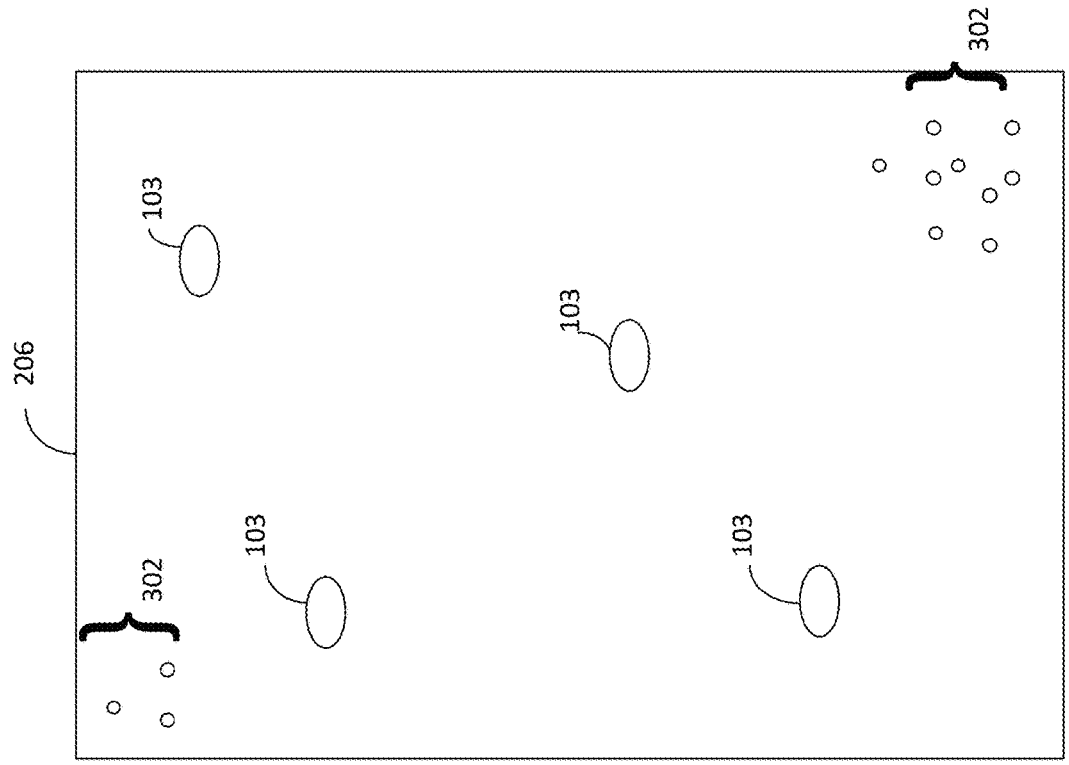
FIGS. 3A and 3B illustrate example views of a window of a checkout workstation. In particular.
Figure 3A:
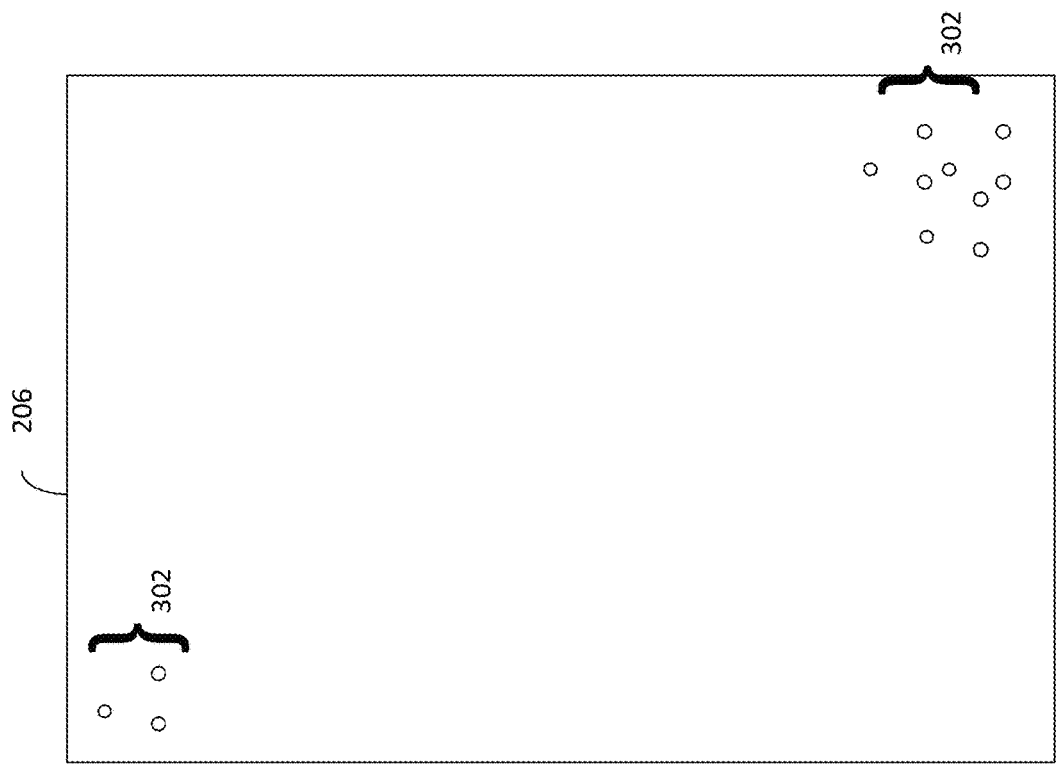

For instance, FIG. 3A illustrates an example window 206 of a checkout workstation 104 including initial threshold contamination 302, which may be used as a control image. The initial threshold contamination 302 may include dirt, dust, or other markings already present on the checkout workstation 104 prior to exposure to any droplets 103 associated with a sneeze or cough. In contrast, FIG. 3B illustrates the example window 206 of the checkout workstation 104 including droplets 103 in addition to the initial threshold contamination 302. Accordingly, the droplet detection application 124 may determine that droplets are present upon the equipment of the checkout workstation 104 based on differences between the images captured by the image sensor 112 and the control images. For instance, blurry, dark, or otherwise obscured portions of the images captured by the image sensor 112 that are not present in the control images (i.e., not part of the threshold contamination 302), in an amount greater than a predetermined threshold, may be indicative of droplets present upon the equipment of the checkout workstation 104. Moreover, in some examples, brighter portions of the images captured by the image sensor 112 that are not part of the threshold contamination 302, in an amount greater than a predetermined threshold, may be indicative of droplets present upon the equipment of the checkout workstation 104, i.e., due to liquid droplets amplifying light present on the window 206. In some examples, the droplet detection application 124 may compare the control images to the images captured by the image sensor 112 based on receiving an indication that the cough or sneeze detection application 126 has detected a cough or sneeze near the checkout workstation 104. Additionally, in some examples, rather than using control images, the droplet detection application 124 may detect that droplets 103 associated with a sneeze or cough are present upon the equipment associated with the checkout workstation 104 based on a change in a real-time image captured by the image sensor 112 that exceeds a threshold rate of change.

In some examples, the droplet detection application 124 may trigger the responsive action based on the quantity or density of droplets that are detected on the equipment associated with the checkout workstation 104, e.g., the droplet detection application 124 may only trigger the responsive action when the quantity or density of droplets present on the equipment associated with the checkout workstation 104 exceeds a certain threshold number of droplets (e.g., since the last disinfection of the checkout workstation 104). Furthermore, in some examples, the droplet detection application 124 may track or count the number of cough or sneeze events during which new liquid droplets are deposited upon the equipment associated with the checkout workstation, and may trigger the responsive action based on the number of such events, e.g., the droplet detection application 124 may only trigger the responsive action when the number of cough or sneeze events during which liquid droplets are deposited upon the equipment exceeds a certain threshold number of events (e.g., since the last disinfection of the checkout workstation 104). Additionally, in some examples, the droplet detection application 124 may trigger the responsive action only when it both detects the presence of droplets on the equipment associated with the checkout workstation 104 and receives an indication that the cough or sneeze detection application 126 has detected a cough or sneeze near the checkout workstation 104.

In some examples, the droplet detection application 124's triggered responsive action may include activating the automatic disinfection component 118 of the checkout workstation 104 discussed above to automatically disinfect the checkout workstation 104 once the individual 102 leaves the checkout workstation. The droplet detection application 124 may determine that the individual 102 has left the checkout workstation 104 based on, e.g., determining that the individual has completed a transaction at the checkout workstation or determining that no transaction activity has occurred at the checkout workstation for greater than a threshold period of time, or by analyzing images captured by the image sensors 112 to determine that the individual is not within the FOV of any of the image sensors 112, or to determine that the individual is greater than the threshold proximity from the checkout workstation 104.

Moreover, in some examples, the droplet detection application 124's triggered responsive action may include sending a signal to an external automatic disinfection component 108, which may be, for instance, a robotic cleaning apparatus configured to automatically travel to the checkout workstation 104 and disinfect the checkout workstation 104 once the individual 102 leaves the checkout workstation 104.

Additionally, in some examples, the droplet detection application 124's triggered responsive action may include generating an alert to be presented to an employee associated with the checkout workstation 104 via an employee computing device 106 that is separate from the checkout workstation 104. For instance, in some examples, the alert may indicate that the employee should close the checkout workstation 104 until it can be disinfected, and/or that the employee should disinfect the checkout workstation 104 (e.g., once the individual 102 has left or otherwise finished using the checkout workstation 104).

Furthermore, in some examples, the droplet detection application 124's triggered responsive action may include automatically closing or locking the checkout workstation 104 to other individuals after the individual 102 leaves the checkout workstation 104 (e.g., until the checkout workstation 104 can be disinfected). For instance, an indicator light associated with the checkout workstation 104 may be activated or deactivated to indicate that the checkout workstation 104 is closed. Moreover, the checkout workstation 104 may be configured to cancel pending transactions, or refuse new transactions, while it is closed or locked. The droplet detection application 124's triggered responsive action may further include re-opening the checkout workstation once it has been disinfected (e.g., automatically or by a store employee).

In some examples, the droplet detection application 124 may determine that the checkout workstation has been disinfected based on receiving an indication from the automatic disinfection component 108 or 118 indicating that the automatic disinfection is complete. Moreover, in some examples, the droplet detection application 124 may determine that the checkout workstation has been disinfected based on receiving an indication from the employee computing device 106 indicating that an employee has confirmed that disinfection is complete. Additionally, in some examples, the droplet detection application 124 may determine that the checkout workstation has been disinfected based on analyzing images captured by the one or more image sensors 112 to determine that a spray bottle is present near the checkout workstation and/or that the spray bottle is spraying disinfectant upon the checkout workstation. Similarly, in some examples, the droplet detection application 124 may determine that the checkout workstation has been disinfected based on analyzing images captured by the one or more image sensors 112 to determine that a wipe event has occurred over the one or more equipment associated with the checkout workstation (i.e., that a disinfectant wipe, or towel sprayed with disinfectant, has moved across an affected portion of the checkout workstation).

Referring now to the cough and/or sneeze detection application 126, as discussed above, executing this cough and/or sneeze detection application 126 may include analyzing image data captured the one or more of the image sensors 112 and/or sound data captured by the one or more microphones 116 to detect indications of coughs or sneezes, and triggering a responsive action based on detecting an indication of a cough or sneeze. Generally speaking, the responsive actions triggered by the cough and/or sneeze detection application may be similar to the responsive actions discussed above as being triggered by the droplet detection application 124 and discussed above.

In some examples, the cough and/or sneeze detection application 126 may analyze the image data captured by the one or more image sensors 112 to detect jerking motions of the head or upper body of an individual 102 near the checkout workstation 104, a repetitive jerking motion associated with an individual 102 near the checkout workstation 104, a covering of the mouth of an individual 102 near the checkout workstation 104 with a hand or arm, and/or a sudden widening of the mouth of an individual 102, all of which may be motions indicative of coughs or sneezes by the individual 102 near the checkout workstation 104. In some examples, executing the cough and/or sneeze detection application 126 may further include analyzing the image data captured by the one or more image sensors 112 to detect whether the individual 102 near the checkout workstation 104 is wearing personal protective equipment (PPE), such as a face covering, and/or whether the individual 102 is wearing PPE properly (e.g., fully covering both nose and mouth). For instance, the cough and/or sneeze detection application 126, in some examples, may not trigger the responsive action if the individual 102 near the checkout workstation 104 is wearing PPE properly. That is, in some cases, even if the individual 102 coughs or sneezes, there may be no need to trigger a responsive action such as disinfecting or closing the checkout workstation if the individual 102 is wearing PPE properly during the cough or sneeze, because the PPE may stop the particles from the cough or sneeze from reaching the checkout workstation 104.

Additionally, in some examples, the cough and/or sneeze detection application 126 may analyze the sound data captured by microphones 116 to detect sounds indicative of coughs or sneezes. For instance, in some examples, the cough and/or sneeze detection application 126 may compare sound data captured by microphones to reference sounds associated with coughs or sneezes. Moreover, in some examples, the cough and/or sneeze detection application 126 may use a machine learning model to identify sounds associated with coughs or sneezes. For instance, the cough and/or sneeze detection application 126 may train a machine learning model to identify sounds of coughs or sneezes using training data that includes sounds of known coughs and/or sneezes detected by the microphones 116 (or by other microphones), and may apply the trained machine learning model to sound data detected by the microphones 116 to detect new coughs and/or sneezes in the sound data.

Furthermore, in some examples, the cough and/or sneeze detection application 126 may analyze the sound data captured by two or more microphones 116 in different positions (e.g., at opposite sides of the checkout workstation 104, as shown in FIG. 8 below) to detect a location or direction of an individual 102 who has coughed or sneezed. For instance, the cough and/or sneeze detection application 126 may compare times at which sounds associated with the same cough or sneeze arrive at each of the microphones in order to triangulate the location (or direction) from which the sound of the sneeze originates. In some examples, the cough and/or sneeze detection application 126 may only trigger the responsive action based on coughs or sneezes originating from certain locations or directions. For instance, if the cough or sneeze originates from further than a threshold distance (e.g., six feet, ten feet, etc.) from the checkout workstation, there may be no need to trigger a responsive action such as disinfecting or closing the checkout workstation. As another example, depending on the configuration of the checkout workstation, a cough or sneeze occurring behind a checkout workstation 104 may not produce droplets that will land on portions of the checkout workstation 104 that will be touched by future users (e.g., the droplets may simply hit the back of the checkout workstation 104, which may not be typically touched by a user). Accordingly, if the cough or sneeze originates from behind the checkout workstation, there may be no need to trigger a responsive action such as disinfecting or closing the checkout workstation.

In some examples, the cough and/or sneeze detection application 126 may track or count the number of indications of coughs and/or sneezes that are detected, and may trigger the responsive action based on the number of such events, e.g., the cough and/or sneeze detection application 126 may only trigger the responsive action when the number of cough or sneeze events during which liquid droplets are deposited upon the equipment exceeds a certain threshold number of events (e.g., since the last disinfection of the checkout workstation 104). Additionally, in some examples, the cough and/or sneeze detection application 126 may trigger the responsive action only when it both detects the presence of droplets on the equipment associated with the checkout workstation 104 and receives an indication that the droplet detection application 124 has detected the presence of droplets on equipment associated with the checkout workstation 104.

Additionally, in some examples, the machine-readable instructions stored in the memory 122 may include instructions for monitoring the checkout workstation 104 for indications that disinfections of the checkout workstation 104 have occurred with a frequency greater than a threshold frequency (e.g., to meet a requirement that the checkout workstation 104 be disinfected at predetermined time intervals, such as every five minutes, every thirty minutes, every hour, etc.), regardless of whether a cough or sneeze has occurred. Similarly, in some examples, the machine-readable instructions stored in the memory 122 may include instructions for monitoring the number of users who use the checkout workstation 104 (e.g., based on a number of transactions processed at the checkout workstation 104, and/or based on data from the image sensors 112 indicating various user faces), and monitoring the checkout workstation 104 for indications that disinfections of the checkout workstation 104 have occurred each time the number of users who have used the checkout workstation since the last disinfection of the checkout workstation 104 exceeds a threshold number (e.g., such that a disinfection occurs every five users, every ten users, every twenty users, etc.), regardless of whether a cough or sneeze has occurred. As another example, the machine-readable instructions stored in the memory 122 may include instructions for monitoring the amount of time each user uses the checkout workstation 104 (e.g., based on a log of the length of each transaction processed at the checkout workstation 104, and/or based on data from the image sensors 112 indicating times or lengths of time when any users are within proximity of the checkout workstation 104), as well as the collective total amount of time that users have used the checkout workstation 104, and monitoring the checkout workstation 104 for indications that disinfections of the checkout workstation 104 have occurred each time the collective amount of time that users have used the checkout workstation since the last disinfection of the checkout workstation 104 exceeds threshold amount of time (e.g., such that there is a disinfection of the checkout workstation 104 each time there is a collective ten minutes, fifteen minutes, twenty minutes, etc., of use of the checkout workstation 104 between various users), regardless of whether a cough or sneeze has occurred.

For instance, these instructions may include instructions for triggering a responsive action based on determining that the frequency of the disinfections of the checkout workstation 104 is below the threshold frequency, based on determining that disinfections of the checkout workstation 104 are not occurring each time the number of users who have used the checkout workstation 104 since the last disinfection exceeds the threshold number of users, and/or based on determining that disinfections of the checkout workstation 104 are not occurring each time the collective time that various use the checkout workstation 104 exceeds the threshold amount of time, regardless of whether a cough or sneeze has occurred. In some examples, the responsive action may include one or more of generating a notification for an employee associated with the checkout workstation 104 to disinfect the checkout workstation 104, causing the automatic disinfection component 108 or 118 to disinfect the checkout workstation, and/or closing the checkout workstation 104 until it can be disinfected.

Figure 4:
FIG. 4 illustrates a block diagram of an example process as may be implemented by the system of FIG. 1, for implementing example methods and/or operations described herein, including droplet detection methods.
Figure 4:

FIG. 4 illustrates a block diagram of an example process 400 as may be implemented by the system of FIG. 1, for implementing example methods and/or operations described herein, e.g., including droplet detection methods discussed as being performed by the droplet detection application 124 of the checkout workstation 104. At block 402, one or more images may be captured by an image sensor associated with a checkout workstation. At block 404, the images may be analyzed to detect an indication that droplets associated with a sneeze and/or a cough are present upon equipment associated with the checkout workstation. At block 406, a disinfection of the checkout workstation (or other responsive action, such as closing the checkout workstation) may be triggered based on the detected indication that droplets associated with a sneeze and/or cough are present upon the equipment associated with the checkout workstation.

Figure 5:
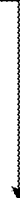
FIG. 5 illustrates a block diagram of an example process as may be implemented by the system of FIG. 1, for implementing example methods and/or operations described herein, including cough and/or sneeze detection methods using image data.
Figure 5:

FIG. 5 illustrates a block diagram of an example process 500 as may be implemented by the system of FIG. 1, for implementing example methods and/or operations described herein, e.g., including cough and/or sneeze detection methods using image data discussed as being performed by the cough and/or sneeze detection application 126 of the checkout workstation 104. At block 502, one or more images of an individual within a threshold proximity of a checkout workstation may be captured by an image sensor associated with the checkout workstation. At block 504, the images may be analyzed to detect motions by the individual indicative of a sneeze or a cough. At block 506, a disinfection of the checkout workstation (or other responsive action, such as closing the checkout workstation) may be triggered based on the detected motions of the individual indicative of the sneeze or cough.

Figure 6:
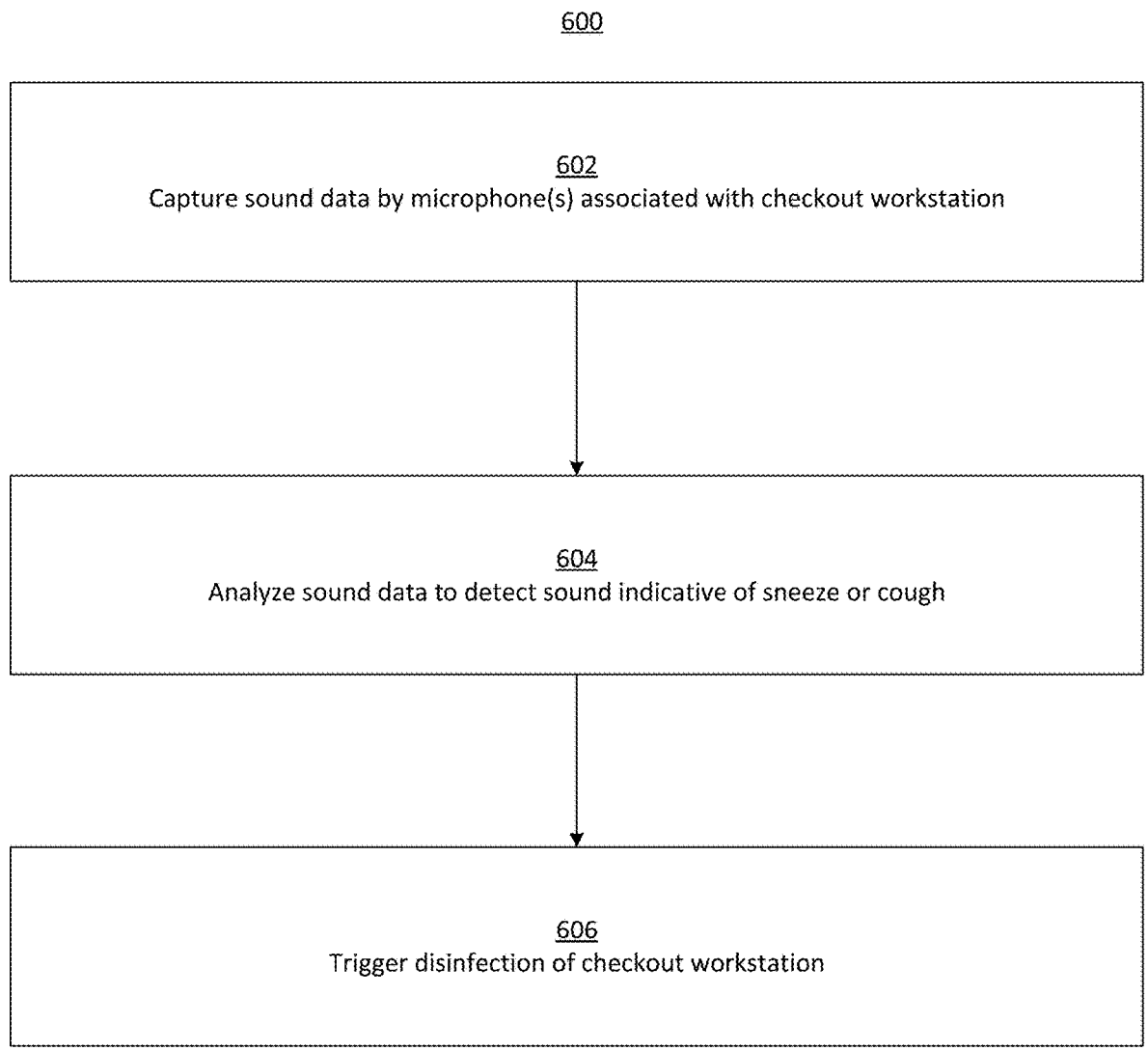
FIG. 6 illustrates a block diagram of an example process as may be implemented by the system of FIG. 1, for implementing example methods and/or operations described herein, including cough and/or sneeze detection methods using microphone data.

FIG. 6 illustrates a block diagram of an example process 600 as may be implemented by the system of FIG. 1, for implementing example methods and/or operations described herein, e.g., including cough and/or sneeze detection methods using microphone data discussed as being performed by the cough and/or sneeze detection application 126 of the checkout workstation 104. At block 602, sound data may be captured by one or more microphones associated with a checkout workstation. At block 604, the sound data may be analyzed to detect sounds indicative of sneezes and/or coughs. At block 606, a disinfection of the checkout workstation (or other responsive action, such as closing the checkout workstation) may be triggered based on the detected sounds indicative of the sneeze or cough.

Figure 7:
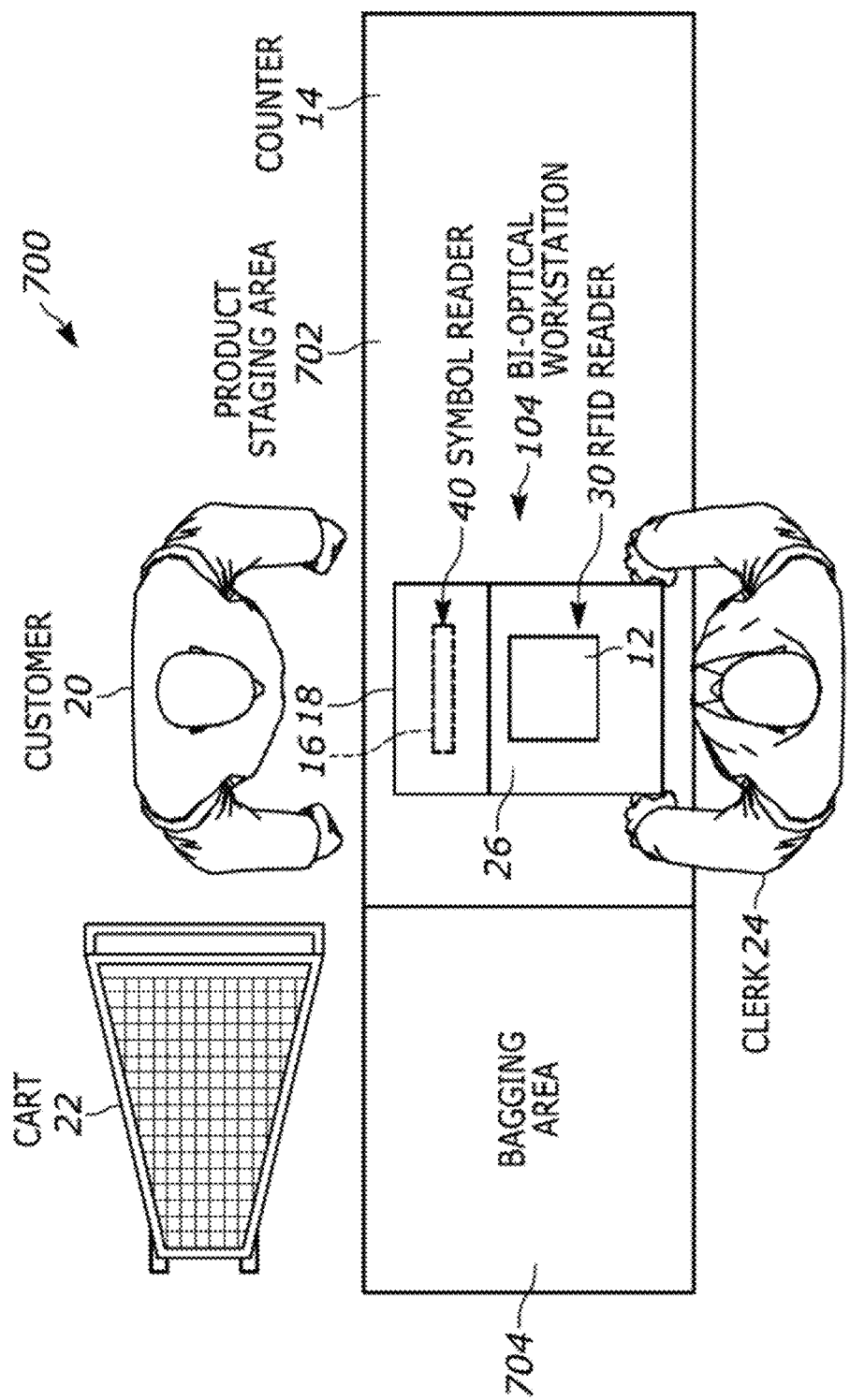
FIG. 7 is a schematic, overhead view of an exemplary bi-optical checkout workstation at a retail checkout counter, for implementing the example methods and/or operations described herein.

Turning now to FIG. 7, depicted therein is an example retail checkout system 700 that includes a dual window, multi-plane, bi-optical, point-of-transaction, retail checkout workstation 104 used by retailers at a retail checkout counter 14 in an aisle to process transactions involving the purchase of retail products associated with, or bearing, an identifying target, such as a barcode or other symbol. In a typical retail venue, a plurality of such workstations 104 is arranged in a plurality of checkout aisles. As best seen in FIG. 8, the workstation 104 has a generally horizontal, planar, generally rectangular, bed window 12 supported by a horizontal bed 26. The bed window 12 is either elevated, or set flush, with the counter 14. A vertical or generally vertical, i.e., slightly tilted, (referred to as "upright" hereinafter) planar, generally rectangular, tower window 16 is set flush with, or, as shown, recessed into, a raised tower 18 above the counter 14. As discussed above, in some examples, microphones 116 may positioned on opposite sides of the tower 18. The workstation 104 either rests directly on the counter 14, or preferably, rests in a cutout or well formed in the counter 14. Both the bed and tower windows 12, 16 are typically positioned to face and be accessible to a clerk 24 (FIG. 7) standing at one side of the counter 14 for enabling the clerk 24 to interact with the workstation 104. Alternatively, in a self-service checkout, the bed and tower windows 12, 16 are typically positioned to face and be accessible to a customer 20.

FIG. 7 also schematically depicts that a product staging area 702 is located on the counter 14 at one side of the workstation 104. The products are typically placed on the product staging area 702 by the customer 20 standing at the opposite side of the counter. The customer 20 typically retrieves the individual products for purchase from a shopping cart 22 or basket for placement on the product staging area 102. A non-illustrated conveyor belt could be employed for conveying the products to the clerk 24.

FIG. 7 schematically depicts that the workstation 104 has a bar code symbol reader 40, for example, a plurality of imaging readers, each including a solid-state imager for capturing light passing through either or both windows 12, 16 from a one- or two-dimensional symbol over an imaging field of view (FOV) 42. In typical use, the clerk 24 may process each product bearing a UPC symbol thereon, past the windows 12, 16 by swiping the product across a respective window, or by presenting the product by holding it momentarily steady at the respective window, before passing the product to a bagging area 704 that is located at the opposite side of the workstation 104. The symbol may be located on any of the top, bottom, right, left, front and rear, sides of the product, and at least one, if not more, of the imagers will capture the return light returning from the symbol through one or both windows 12, 16 as an image.

In some examples, the workstation 104 may further include an RFID reader 30 that detects return RF energy returning from RFID tags associated with the products passing through the workstation 104 past either or both windows 12, 16. Although the workstation 104 has been illustrated as a dual-window workstation, it will be understood that the readers 30 and/or 40 could be installed in other types of workstations, for example, a flat bed scanner having a single horizontal window, or a vertical slot scanner having a single upright window. As previously mentioned, either or both windows 12, 16 is transmissive to light, for example, is constituted of glass or plastic. In the case of imaging readers, an illumination source emits illumination light in one direction through the windows 12, 16, and the return illumination light that is reflected and/or scattered from the symbol passes in the opposite direction to the imagers. In the case of moving laser beam readers, a laser emits laser light in one direction through the windows 12, 16, and the return laser light that is reflected and/or scattered from the symbol passes in the opposite direction to a photodetector. The bed 26 and the tower 18 of the workstation 104 together comprise a housing or chassis for supporting the windows 12, 16.

The above description refers to a block diagram of the accompanying drawings. Alternative implementations of the example represented by the block diagram includes one or more additional or alternative elements, processes and/or devices. Additionally or alternatively, one or more of the example blocks of the diagram may be combined, divided, re-arranged or omitted. Components represented by the blocks of the diagram are implemented by hardware, software, firmware, and/or any combination of hardware, software and/or firmware. In some examples, at least one of the components represented by the blocks is implemented by a logic circuit. As used herein, the term "logic circuit" is expressly defined as a physical device including at least one hardware component configured (e.g., via operation in accordance with a predetermined configuration and/or via execution of stored machine-readable instructions) to control one or more machines and/or perform operations of one or more machines. Examples of a logic circuit include one or more processors, one or more coprocessors, one or more microprocessors, one or more controllers, one or more digital signal processors (DSPs), one or more application specific integrated circuits (ASICs), one or more field programmable gate arrays (FPGAs), one or more microcontroller units (MCUs), one or more hardware accelerators, one or more special-purpose computer chips, and one or more system-on-a-chip (SoC) devices. Some example logic circuits, such as ASICs or FPGAs, are specifically configured hardware for performing operations (e.g., one or more of the operations described herein and represented by the flowcharts of this disclosure, if such are present). Some example logic circuits are hardware that executes machine-readable instructions to perform operations (e.g., one or more of the operations described herein and represented by the flowcharts of this disclosure, if such are present). Some example logic circuits include a combination of specifically configured hardware and hardware that executes machine-readable instructions. The above description refers to various operations described herein and flowcharts that may be appended hereto to illustrate the flow of those operations. Any such flowcharts are representative of example methods disclosed herein. In some examples, the methods represented by the flowcharts implement the apparatus represented by the block diagrams. Alternative implementations of example methods disclosed herein may include additional or alternative operations. Further, operations of alternative implementations of the methods disclosed herein may combined, divided, re-arranged or omitted. In some examples, the operations described herein are implemented by machine-readable instructions (e.g., software and/or firmware) stored on a medium (e.g., a tangible machine-readable medium) for execution by one or more logic circuits (e.g., processor(s)). In some examples, the operations described herein are implemented by one or more configurations of one or more specifically designed logic circuits (e.g., ASIC(s)). In some examples the operations described herein are implemented by a combination of specifically designed logic circuit(s) and machine-readable instructions stored on a medium (e.g., a tangible machine-readable medium) for execution by logic circuit(s).

As used herein, each of the terms "tangible machine-readable medium," "non-transitory machine-readable medium" and "machine-readable storage device" is expressly defined as a storage medium (e.g., a platter of a hard disk drive, a digital versatile disc, a compact disc, flash memory, read-only memory, random-access memory, etc.) on which machine-readable instructions (e.g., program code in the form of, for example, software and/or firmware) are stored for any suitable duration of time (e.g., permanently, for an extended period of time (e.g., while a program associated with the machine-readable instructions is executing), and/or a short period of time (e.g., while the machine-readable instructions are cached and/or during a buffering process)). Further, as used herein, each of the terms "tangible machine-readable medium," "non-transitory machine-readable medium" and "machine-readable storage device" is expressly defined to exclude propagating signals. That is, as used in any claim of this patent, none of the terms "tangible machine-readable medium," "non-transitory machine-readable medium," and "machine-readable storage device" can be read to be implemented by a propagating signal.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. Additionally, the described embodiments/examples/implementations should not be interpreted as mutually exclusive, and should instead be understood as potentially combinable if such combinations are permissive in any way. In other words, any feature disclosed in any of the aforementioned embodiments/examples/implementations may be included in any of the other aforementioned embodiments/examples/implementations.

The benefits, advantages, solutions to problems, and any element(s) that may cause any benefit, advantage, or solution to occur or become more pronounced are not to be construed as a critical, required, or essential features or elements of any or all the claims. The claimed invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separately claimed subject matter.

The invention claimed is:

1. A method, comprising:
   capturing, by an image sensor associated with a checkout workstation, one or more images;
   analyzing, by one or more processors, the images captured by the image sensor associated with the checkout workstation, to detect an indication that one or more droplets associated with a sneeze or cough are present upon one or more equipment associated with the checkout workstation; and
   triggering, by the one or more processors, a disinfection of the checkout workstation responsive to detecting the indication that the one or more droplets associated with the sneeze or cough are present upon the one or more equipment associated with the checkout workstation.

2. The method of claim 1, wherein triggering the disinfection of the checkout workstation includes triggering an alert for an employee associated with the checkout workstation indicating that the checkout workstation should be disinfected.

3. The method of claim 1, further comprising:
   capturing, by one or more microphones associated with the checkout workstation, sound data associated with the checkout workstation;
   analyzing, by the one or more processors, the sound data associated with the checkout workstation to detect a sound indicative of a sneeze or cough; and
   wherein triggering the disinfection of the checkout workstation is further responsive to determining the indication of the sound indicative of the sneeze or cough.

4. The method of claim 3, wherein a first microphone of the one or more microphones associated with the checkout workstation is positioned on a first side of the checkout workstation, and wherein a second microphone of the one or more microphones associated with the checkout workstation is positioned on a second side of the checkout workstation, the second side being opposite the first side, and further comprising:
   comparing, by the one or more processors, the sound indicative of the sneeze or cough captured by the first microphone and the second microphone to determine whether the sneeze or cough originates from the first side, the second side, or a central point between the first side and the second side; and
   wherein triggering the disinfection of the checkout workstation is further responsive to determining that the sneeze or cough originates from a central point between the first side and the second side.

5. The method of claim 1, further comprising:
   capturing, by one or more microphones associated with the checkout workstation, indications of sound data associated with the checkout workstation;
   analyzing, by the one or more processors, the sound data associated with the checkout workstation to detect a sound indicative of a sneeze or cough; and
   wherein the image sensor is activated for capturing images responsive to detecting the sound indicative of the sneeze or cough.

6. The method of claim 1, further comprising closing the checkout workstation responsive to detecting the indication that the one or more droplets associated with the sneeze or cough are present upon the one or more equipment associated with the checkout workstation.

7. The method of claim 6, further comprising re-opening the checkout workstation responsive to determining that the one or more equipment associated with the checkout workstation have been disinfected.

8. The method of claim 7, wherein determining that the one or more equipment associated with the checkout workstation have been disinfected includes:
   detecting, by the image sensor associated with the checkout workstation, that a spray bottle is present near the checkout workstation.

9. The method of claim 7, wherein determining that the one or more equipment associated with the checkout workstation have been disinfected includes:
   detecting, by the image sensor associated with the checkout workstation, that a wipe event has occurred over the one or more equipment associated with the checkout workstation.

10. The method of claim 1, further comprising:
    shining, by an ultraviolet (UV) light source, UV light upon the affected one or more equipment associated with the checkout workstation; and
    determining that the one or more droplets present upon the affected one or more equipment associated with the checkout workstation are associated with a sneeze or cough based on fluorescence of the one or more droplets in the UV light.

11. The method of claim 1, wherein the image sensor is a first image sensor;
    and wherein the first image sensor is activated for detecting indications of droplets associated with the sneeze or cough responsive to a second image sensor associated with the checkout workstation detecting a motion of an individual using with the checkout workstation indicative of a cough or sneeze.

12. The method of claim 1, wherein the image sensor is a variable-focus image sensor, and wherein detecting the indication that one or more droplets associated with a sneeze or cough are present upon one or more equipment associated with the checkout workstation includes:
    cycling, by the variable-focus image sensor, through the focal plane of a window of the checkout workstation to determine that one or more droplets associated with a sneeze or cough are present upon on the window of the checkout workstation.

13. The method of claim 1, wherein detecting the indication that one or more droplets associated with a sneeze or cough are present upon one or more equipment associated with the checkout workstation includes detecting a change in a refractive index of a window of the checkout workstation.

14. The method of claim 1, wherein detecting the indication that one or more droplets associated with a sneeze or cough are present upon one or more equipment associated with the checkout workstation includes comparing one or more control images to one or more images captured by the image sensor associated with the checkout workstation.

15. The method of claim 14, wherein the one or more control images are images of the checkout workstation that do not include droplets associated with the sneeze or cough present upon the one or more equipment associated with the checkout workstation.

16. The method of claim 1, further comprising:
    tracking, by one or more processors, one or more of (i) a quantity of droplets present upon the one or more equipment associated with the checkout workstation or (ii) a quantity of events during which droplets are deposited upon the one or more equipment associated with the checkout workstation; and
    wherein triggering the disinfection of the checkout workstation is further responsive to one or more of (i) the quantity of droplets present upon the one or more equipment associated with the checkout workstation exceeding a threshold quantity of droplets or (ii) the quantity of events during which droplets are deposited upon the one or more equipment associated with the checkout workstation exceeding a threshold quantity of events.

17. The method of claim 1, further comprising:
illuminating an edge of a window of the checkout workstation for the capture of the one or more images.

18. A method, comprising:
capturing, by an image sensor associated with a checkout workstation, one or more images;
analyzing, by one or more processors, the images captured by the image sensor associated with the checkout workstation, to detect an indication that one or more droplets associated with a sneeze or cough are present upon one or more equipment associated with the checkout workstation; and
triggering, by the one or more processors, responsive to detecting the indication that the one or more droplets associated with the sneeze or cough are present upon the one or more equipment associated with the checkout workstation, an automatic dissemination, by a disinfection device associated with the checkout workstation, of disinfectant over the affected one or more equipment for a threshold period of time for disinfecting the one or more equipment.

19. The method of claim 18, wherein the disinfection device includes an ultraviolet (UV) disinfection light directed upon the affected one or more equipment, and wherein automatic dissemination of disinfectant over the affected one or more equipment includes automatically activating the UV disinfection light directed upon the affected one or more equipment for the threshold period of time.

20. The method of claim 18, wherein the disinfection device includes a liquid disinfectant sprayer directed upon the affected one or more equipment, and wherein automatic dissemination of disinfectant over the affected one or more equipment includes automatically activating the liquid disinfectant sprayer to spray liquid disinfectant upon the affected one or more equipment for the threshold period of time.

21. The method of claim 18, further comprising:
capturing, by one or more microphones associated with the checkout workstation, indications of sound data associated with the checkout workstation;
analyzing, by the one or more processors, the sound data associated with the checkout workstation to detect a sound indicative of a sneeze or cough; and
wherein triggering the automatic dissemination of disinfectant over the affected one or more equipment of the checkout workstation is further responsive to detecting the sound indicative of the sneeze or cough.

22. The method of claim 21, wherein a first microphone of the one or more microphones associated with the checkout workstation is positioned on a first side of the checkout workstation, and wherein a second microphone of the one or more microphones associated with the checkout workstation is positioned on a second side of the checkout workstation, the second side being opposite the first side, and further comprising:
comparing, by the one or more processors, the sound indicative of the sneeze or cough captured by the first microphone and the second microphone to determine whether the sneeze or cough originates from the first side, the second side, or a central point between the first side and the second side; and
wherein the image sensor is activated for capturing images further responsive to determining that the sneeze or cough originates from a central point between the first side and the second side.

23. The method of claim 18, further comprising:
capturing, by one or more microphones associated with the checkout workstation, indications of sound data associated with the checkout workstation;
analyzing, by the one or more processors, the sound data associated with the checkout workstation to detect a sound indicative of a sneeze or cough; and
wherein the image sensor is activated for capturing images responsive to detecting the sound indicative of the sneeze or cough.

24. The method of claim 18, further comprising closing the checkout workstation responsive to detecting the indication that the one or more droplets associated with the sneeze or cough are present upon the one or more equipment associated with the checkout workstation.

25. The method of claim 24, further comprising re-opening the checkout workstation responsive to the automatic dissemination, by the disinfection device associated with the checkout workstation, of disinfectant over the affected one or more equipment for the threshold period of time.

26. The method of claim 18, further comprising:
shining, by a UV light source, UV light upon the affected one or more equipment associated with the checkout workstation; and
determining that the one or more droplets present upon the affected one or more equipment associated with the checkout workstation are associated with a sneeze or cough based on fluorescence of the one or more droplets in the UV light.

27. The method of claim 18, wherein the image sensor is a variable-focus image sensor, and wherein detecting the indication that one or more droplets associated with a sneeze or cough are present upon one or more equipment associated with the checkout workstation includes:
cycling, by the variable-focus image sensor, through the focal plane of a window of the checkout workstation to determine that one or more droplets associated with a sneeze or cough are present upon on the window of the checkout workstation.

28. The method of claim 18, wherein detecting the indication that one or more droplets associated with a sneeze or cough are present upon one or more equipment associated with the checkout workstation includes detecting a change in a refractive index of a window of the checkout workstation.

29. The method of claim 18, wherein detecting the indication that one or more droplets associated with a sneeze or cough are present upon one or more equipment associated with the checkout workstation includes comparing one or more control images to one or more images captured by the image sensor associated with the checkout workstation.

30. The method of claim 29, wherein the one or more control images are images of the checkout workstation that do not include droplets associated with the sneeze or cough present upon the one or more equipment associated with the checkout workstation.

31. The method of claim 18, further comprising:
tracking, by one or more processors, one or more of (i) a quantity of droplets present upon the one or more equipment associated with the checkout workstation or (ii) a quantity of events during which droplets are deposited upon the one or more equipment associated with the checkout workstation; and wherein triggering the automatic dissemination of disinfectant over the affected one or more equipment is further responsive to one or more of (i) the quantity of droplets present upon the one or more equipment associated with the checkout workstation exceeding a threshold quantity of droplets or (ii) the quantity of events during which droplets are deposited upon the one or more equipment associated with the checkout workstation exceeding a threshold quantity of events.

32. The method of claim 18, further comprising:
illuminating an edge of a window of the checkout workstation for the capture of the one or more images.

\* \* \* \* \*